United States Patent [19]

Smithwick, Jr. et al.

[11] 4,331,593
[45] * May 25, 1982

[54] ANALGESIC COMPOUNDS

[76] Inventors: Edward L. Smithwick, Jr.; Robert C. A. Frederickson, both of Indianapolis; Robert T. Shuman, Greenwood, all of Ind.

[*] Notice: The portion of the term of this patent subsequent to Mar. 31, 1998, has been disclaimed.

[21] Appl. No.: 202,514

[22] Filed: Oct. 31, 1980

Related U.S. Application Data

[62] Division of Ser. No. 838,516, Oct. 3, 1977, Pat. No. 4,264,491.

[51] Int. Cl.³ .................................................. C07C 103/52
[52] U.S. Cl. .................................................. 260/112.5 E
[58] Field of Search .................................... 260/112.5 R

[56] References Cited

U.S. PATENT DOCUMENTS 4,264,491 4/1981 Smithwick, Jr. et al. ..... 260/112.5 R

Primary Examiner—Delbert R. Phillips
Attorney, Agent, or Firm—William C. Martens, Jr.; Arthur R. Whale

[57] ABSTRACT

Compounds of the formula

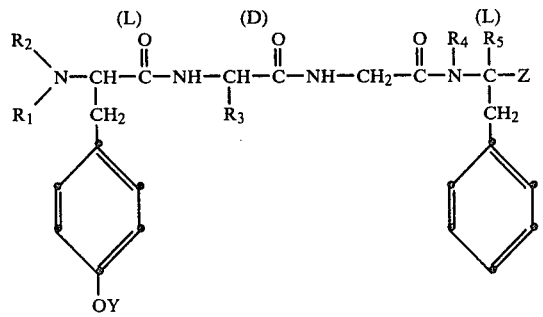

and pharmaceutically acceptable non-toxic acid addition salts thereof, in which L and D, when applicable, define the chirality;

$R_1$ and $R_2$ independently are hydrogen or $C_1$–$C_3$ primary alkyl;

$R_3$ is $C_1$–$C_4$ primary or secondary alkyl or —$CH_2CH_2$—S—$CH_3$;

$R_4$ is hydrogen or $C_1$–$C_3$ primary alkyl;

$R_5$ is hydrogen or $C_1$–$C_3$ primary alkyl;

Y is hydrogen or acetyl; and

Z is

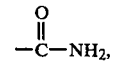

—$CH_2OH$, or —$CN$; subject to the limitation that no more than one of $R_4$ and $R_5$ is $C_1$–$C_3$ primary alkyl; are useful analgesic agents.

32 Claims, No Drawings

ANALGESIC COMPOUNDS

This is a division, of application Ser. No. 838,516 filed Oct. 3, 1977, now U.S. Pat. No. 4,264,491 issued Apr. 28, 1981.

BACKGROUND OF THE INVENTION

This invention relates to a novel class of compounds which exhibit analgesic activity upon parenteral administration.

Recently, endogenous substances having morphine-like properties have been extracted from mammalian brain or csf. These substances, named enkephalin, have been identified by Hughes et al., Nature, 258, 577 (1975) as pentapeptides having the following sequences:

H-Tyr-Gly-Gly-Phe-Met-OH
H-Tyr-Gly-Gly-Phe-Leu-OH.

These compounds are referred to as methionine-enkephalin and leucine-enkephalin, respectively.

Although these compounds have been shown to exhibit analgesic activity in mice upon administration intracerebroventricularly [Buscher et al., Nature, 261, 423 (1976)], they are practically devoid of any useful analgesic activity when administered parenterally.

A novel class of compounds has now been discovered. These compounds exhibit significant and demonstrable analgesic activity when administered systemically. It is to this class of compounds that this invention is directed.

SUMMARY OF THE INVENTION

Thus, this invention relates to a class of compounds having the formula

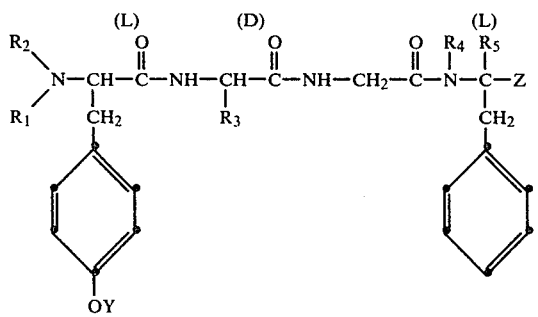

and pharmaceutically acceptable non-toxic acid addition salts thereof, in which L and D, when applicable, define the chirality;

$R_1$ and $R_2$ independently are hydrogen or $C_1$–$C_3$ primary alkyl;

$R_3$ is $C_1$–$C_4$ primary or secondary alkyl or —CH$_2$CH$_2$—S—CH$_3$;

$R_4$ is hydrogen or $C_1$–$C_3$ primary alkyl;

$R_5$ is hydrogen or $C_1$–$C_3$ primary alkyl;

Y is hydrogen or acetyl; and

Z is

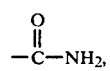

—CH$_2$OH, or —CN; subject to the limitation that no more than one of $R_4$ and $R_5$ is $C_1$–$C_3$ primary alkyl.

DETAILED DESCRIPTION OF THE INVENTION

As indicated above, the compounds of this invention have the following structure:

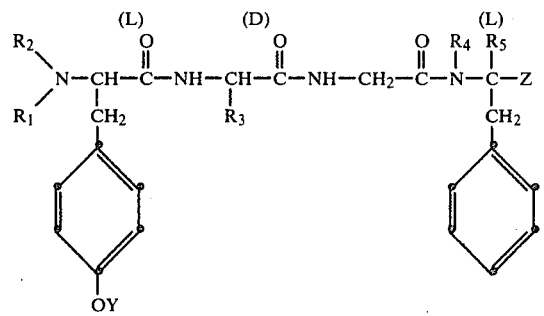

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are the primary amide, primary alcohol, or nitrile derivatives of specifically defined tetrapeptides. The stereoconfiguration of the compounds of this invention is an essential feature thereof. For the sake of convenience, the amino acid residues of the modified tetrapeptides of this invention are numbered sequentially beginning with the residue at the terminal amino function. The chirality of the amino acid residues, reading from Position 1 through Position 3, is L, D, and none. The residue in Position 3 is a glycine moiety, and, thus, no chirality as to this residue exists. As to Position 4 (the C-terminal position) which is a primary amide, a primary alcohol, or a nitrile, its chirality is defined as that which is consistent with the corresponding putative L-amino acid residue.

The groups $R_1$, $R_2R_4$, and $R_5$ as used herein are defined to include the group "$C_1$–$C_3$ primary alkyl". By the term "$C_1$–$C_3$ primary alkyl" is intended methyl, ethyl, and n-propyl.

The group $R_3$ appearing in the above structural formula is defined to include the group "$C_1$–$C_4$ primary or secondary alkyl". By the term "$C_1$–$C_4$ primary or secondary alkyl" is meant methyl, ethyl, n-propyl, isopropyl, n-butyl, isobutyl, and sec-butyl.

With respect to the particular residues in each of the positions of the modified tetrapeptides of this invention, the following considerations prevail:

(A). Position 1

This position represents the amino-terminal portion of the peptide. The residue is that which results from L-tyrosine or L-(O-acetyl)tyrosine. In either instance, the residue can be N-unsubstituted, in which case both $R_1$ and $R_2$ are hydrogen. Moreover, the residue can be substituted by one or two $C_1$-$C_3$ primary alkyl groups, in which case $R_1$ and/or $R_2$ is $C_1$-$C_3$ primary alkyl. Specific illustrations of $C_1$-$C_3$ primary alkyl substitution include N-methyl-, N-ethyl-, N-n-propyl-, N,N-dimethyl, N,N-diethyl, N,N-di-n-propyl, N,-methyl-N-ethyl, N-methyl-N-n-propyl, N-ethyl-N-n-propyl, and the like. Preferably, the tyrosyl or O-acetyltyrosyl residue which is present in Position 1 of the peptide of this invention is N-unsubstituted. Furthermore, it is preferred that the residue is tyrosyl.

(B). Position 2

The amino acid residue which is present in the second position of the peptide of this invention must be the D stereoisomer and is any of several amino acid residues. These include residues derived from D-alanine (Ala) ($R_3$ is methyl), D-α-aminobutyric acid (Abu) ($R_3$ is ethyl), D-norvaline (Nva) ($R_3$ is n-propyl), D-valine (Val) ($R_3$ is isopropyl), D-norleucine (Nle) ($R_3$ is n-butyl), D-leucine (Leu) ($R_3$ is isobutyl), D-isoleucine (Ile) ($R_3$ is sec-butyl), and D-methionine (Met) ($R_3$ is —$CH_2CH_2$—S—$CH_3$). Preferably, the residue is that derived from D-alanine.

(C). Position 3

The amino acid residue present in this position is that derived from glycine (Gly).

(D). Position 4

The residue present in the C-terminal position is that derived from L-phenylalanine (Phe) or the primary alcohol or nitrile derivatives thereof. The residue can be a primary amide (Phe-$NH_2$)

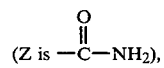

(Z is —$\overset{\overset{O}{\|}}{C}$—$NH_2$), a primary alcohol (Phe-A) (Z is —$CH_2OH$), or a nitrile (Phe-CN) (Z is —CN). A preferred class of compounds is that in which Z is

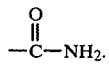

—$\overset{\overset{O}{\|}}{C}$—$NH_2$.

The residue can be either unsubstituted or substituted at the amino nitrogen ($R_4$). In the event that the residue is N-substituted, it is N-methyl, N-ethyl, or N-n-propyl. In addition, in the event that the residue is unsubstituted at the amino nitrogen, it can be substituted at the α-carbon ($R_5$). In such instances, $R_5$ is methyl, ethyl, or n-propyl. The only limitation is that both $R_4$ and $R_5$ cannot be $C_1$-$C_3$ primary alkyl. Preferably, a substituent is present either at the amino nitrogen or the α-carbon, i.e., $R_4$ or $R_5$ is $C_1$-$C_3$ primary alkyl. More preferably, the $C_1$-$C_3$ primary alkyl group is methyl. Thus, highly preferred compounds are those in which $R_4$ or $R_5$ is methyl, and most preferably, those in which $R_4$ is methyl.

In this specification, the following abbreviations, most of which are well known and are commonly used in the art, are employed:

Abu—α-aminobutyric acid
Ala—alanine
Cys—cysteine
Gly—glycine
Hse—homoserine
Ile—isoleucine
Leu—leucine
Met—methionine
Nle—norleucine
Nva—norvaline
Phe—phenylalanine
Phe—$NH_2$—phenylalanine amide
Phe-A—primary alcohol derivative of phenylalanine
Phe-CN—nitrile derivative of phenylalanine
Ser—serine
Tyr—tyrosine
Val—valine
Ac—acetyl
Me—methyl
Et—ethyl
Ip—ispropyl
Pr—n-propyl
Bu—n-butyl
i-Bu—isobutyl
t-Bu—t-butyl
s-Bu—sec-butyl
BOC—t-butyloxycarbonyl
Bzl—benzyl
DCC—N,N'-dicylohexylcarbodiimide
HBT—1-hydroxybenzotriazole
DMF—N,N-dimethylformamide
TFA—trifluoroacetic acid
THF—tetrahydrofuran
DEAE—diethylaminoethyl Examples of typical compounds of this invention include the following:

H-L-Tyr-D-Ala-Gly-L-Phe-$NH_2$;
H-L-Tyr-D-Ala-Gly-L-Phe-A;
H-L-Tyr-D-Abu-Gly-L-Phe-CN;
H-L-Tyr-D-Abu-Gly-L-Phe-$NH_2$;
H-L-Tyr-D-Nva-Gly-L-Phe-$NH_2$;
H-L-Tyr-D-Nva-Gly-L-Phe-A;
H-L-Tyr-D-Val-Gly-L-Phe-$NH_2$;
H-L-Tyr-D-Val-Gly-L-Phe-CN;
H-L-Tyr-D-Nle-Gly-L-Phe-$NH_2$;
H-L-Tyr-D-Nle-Gly-L-Phe-A;
H-L-Tyr-D-Leu-Gly-L-Phe-$NH_2$;
H-L-Tyr-D-Leu-Gly-L-Phe-CN;
H-L-Tyr-D-Ile-Gly-L-Phe-$NH_2$;
H-L-Tyr-D-Ile-Gly-L-Phe-A;
H-L-Tyr-D-Ala-Gly-L-(N-Et)Phe-$NH_2$;
H-L-Tyr-D-Ala-Gly-L-(N-Pr)Phe-$NH_2$;
H-L-Tyr-D-Ala-Gly-L-(N-Pr)Phe-A;
H-L-Tyr-D-Ala-Gly-L-(α-Me)Phe-$NH_2$;
H-L-Tyr-D-Ala-Gly-L-(N-Me)Phe-$NH_2$;
H-L-Tyr-D-Ala-Gly-L-(α-Et)Phe-$NH_2$;
H-L-Tyr-D-Ala-Gly-L-(N-Me)Phe-CN;
H-L-Tyr-D-Ala-Gly-L-(N-Me)Phe-A;
H-L-Tyr-D-Met-Gly-L-Phe-$NH_2$;
H-L-Tyr-D-Met-Gly-L-(N-Et)Phe-$NH_2$;
H-L-Tyr-D-Met-Gly-L-(N-Me)Phe-$NH_2$;
H-L-Tyr-D-Met-Gly-L-(N-Me)Phe-A;
H-L-Tyr-D-Met-Gly-L-(N-Et)Phe-CN;
H-L-Tyr-D-Met-Gly-L-(α-Et)Phe-$NH_2$;
H-L-Tyr-D-Met-Gly-L-(α-Pr)Phe-$NH_2$;
H-L-Tyr(Ac)-D-Ala-Gly-L-Phe-$NH_2$;
H-L-Tyr(Ac)-D-Ala-Gly-L-(N-Me)Phe-$NH_2$;
H-L-Tyr(Ac)-D-Nle-Gly-L-(α-Me)Phe-$NH_2$;
H-L-Tyr(Ac)-D-Abu-Gly-L-Phe-A;
(N-Me)-L-Tyr-D-Ala-Gly-L-Phe-$NH_2$;
(N,N-Di-Me)-L-Tyr-D-Ala-Gly-L-Phe-$NH_2$;
H-L-Tyr(Ac)-D-Ala-Gly-L-Phe-CN;

(N-Et)-L-Tyr-D-Abu-Gly-L-(N-Et)Phe-NH₂;
(N,N-di-Pr)-L-Tyr-D-Val-Gly-L-(α-Me)Phe-NH₂;
(N-Pr)-L-Tyr-D-Leu-Gly-L-(α-Et)Phe-NH₂;
(N,N-Di-Et)-L-Tyr-D-Met-Gly-L-(α-Pr)Phe-NH₂;
(N-Me,N-Et)-L-Tyr(Ac)-D-Nle-Gly-L-(α-Me)Phe-NH₂;
(N,N-Di-Me)-L-Tyr(Ac)-D-Ile-Gly-L-(α-Et)Phe-NH₂;
(N-Me)-L-Tyr(Ac)-D-Leu-Gly-L-(α-Me)Phe-CN;
(N-Me)-L-Tyr(Ac)-D-Nva-Gly-L-(α-Pr)Phe-A;
(N-Me)-L-Tyr-D-Ala-Gly-L-(α-Me)Phe-NH₂;
(N-Et)-L-Tyr(Ac)-D-Abu-Gly-L-(α-Pr)Phe-NH₂;
(N-Pr)-L-Tyr(Ac)-D-Val-Gly-L-Phe-NH₂;
H-L-Tyr-D-Ala-Gly-L-(α-Me)Phe-CN;
H-L-Tyr-D-Ala-Gly-L-(α-Me)Phe-A;
H-L-Tyr-D-Ala-Gly-L-(α-Et)Phe-A;
H-L-Tyr-D-Ala-Gly-L-(α-Pr)Phe-NH₂;
H-L-Tyr-D-Ala-Gly-L-(α-Pr)Phe-CN;
(N,N-Di-Me)-L-Tyr-D-Ala-Gly-L-(α-Et)Phe-A;
(N,N-Di-Me)-L-Tyr-D-Ala-Gly-L-(N-Me)Phe-NH₂;
(N,N-Di-Et)-L-Tyr-D-Ala-Gly-L-(N-Et)Phe-CN;
(N-Me)-L-Tyr-D-Ala-Gly-L-(N-Me)Phe-A;
(N-Me)-L-Tyr-D-Ala-Gly-L-(N-Me)Phe-NH₂;
(N,N-Di-Me)-L-Tyr-D-Val-Gly-L-(N-Me)Phe-NH₂;
(N,N-Di-Pr)-L-Tyr-D-Ala-Gly-L-(N-Pr)Phe-NH₂;
(N-Me)-L-Tyr-D-Ala-Gly-L-(α-Et)Phe-NH₂;
(N,N-Di-Me)-L-Tyr(Ac)-D-Ala-Gly-L-(N-Et)Phe-CN;
(N,N-Di-Pr)-L-Tyr(Ac)-D-Met-Gly-L-(N-Me)Phe-A;
(N-Et)-L-Tyr(Ac)-D-Met-Gly-L-(N-Pr)Phe-NH₂;
(N-Me)-L-Tyr(Ac)-D-Met-Gly-L-(α-Me)Phe-NH;
and the like.

The compounds of this invention are prepared by routine methods for peptide synthesis. It is possible, during the synthesis of certain of the compounds of this invention, that partial racemization can occur. However, the extent of racemization, should such occur, is not sufficient to seriously alter the analgesic activity of the compounds of this invention.

The methods for preparing the compounds of this invention involve the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by employing techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl (CBz), t-butyloxycarbonyl (BOC), t-amyloxycarbonyl (AOC), p-methoxybenzyloxycarbonyl (MBOC), adamantyloxycarbonyl (AdOC), and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. The carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

The amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of the amino blocking group also can be accomplished by treating the blocked amino acid or peptide with a mixture of HBr or HCl and acetic acid to produce the corresponding hydrobromide or hydrochloride acid addition salt. The particular method or reagent which is employed will depend upon the chemical or physical characteristics of the materials involved in the specific deblocking reaction. It has been discovered, in those instances in which the group $R_4$ is other than hydrogen and a peptide containing at least three amino acid residues is to be deblocked, that it is highly preferred that the peptide be deblocked with trifluoroacetic acid or formic acid to produce the corresponding acid addition salt. The salt can be converted to a more pharmaceutically acceptable form by treatment with a suitable ion exchange resin, such as DEAE Sephadex A25, Amberlyst A27, and the like.

The hydroxy-protecting group present on the tyrosyl residue can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of a tyrosyl residue having a free hydroxyl group.

A preferred specific method for preparing the compounds of this invention involves coupling a separately prepared N-terminal tripeptide with a separately prepared C-terminal phenylalanyl amide

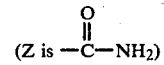

$$(Z \text{ is } -\overset{\overset{\displaystyle O}{\|}}{C}-NH_2)$$

or its corresponding alcohol (Z is $-CH_2OH$) or nitrile (Z is $-CN$) followed by appropriate deblocking of any remaining blocked moieties. Alternatively, the separately prepared C-terminal phenylalanyl compound which is reacted with the N-terminal tripeptide can be structured so as to contain a group which represents a precursor to any of the amide, alcohol, or nitrile moieties. The general sequence, illustrating preparation of a tetrapeptide of this invention, can be depicted as follows. In the sequence, the symbol AA represents the amino acid residue, and the appended number represents the position of the amino acid in the ultimate peptide product sequence.

A. Preparation of the tripeptide segment.

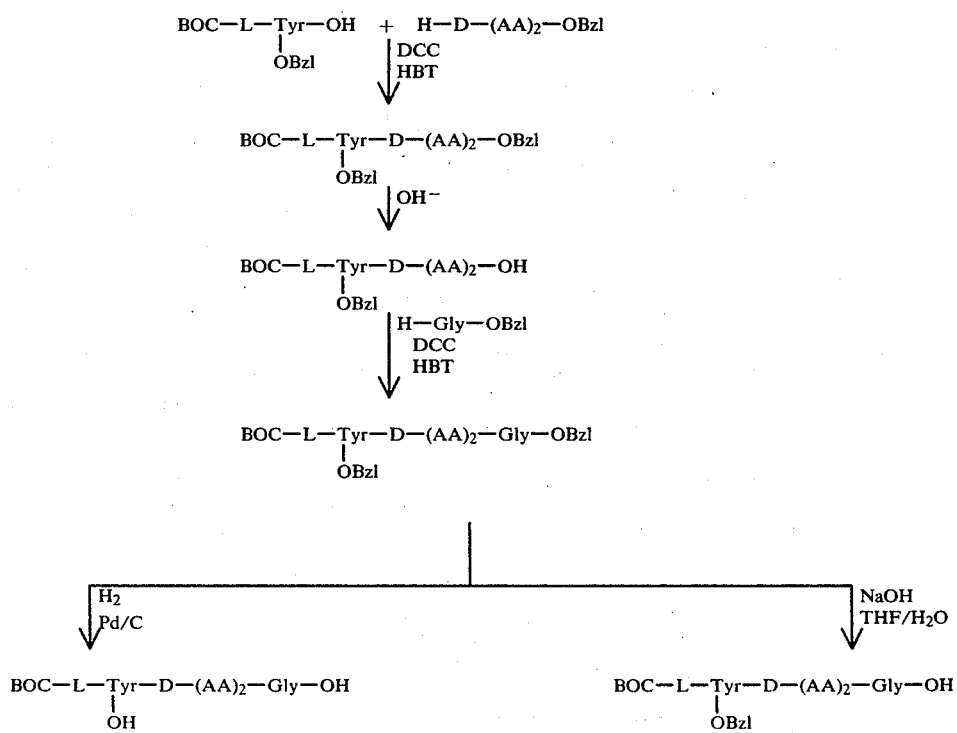

B. Coupling of tripeptide and terminal phenylalanyl moiety.

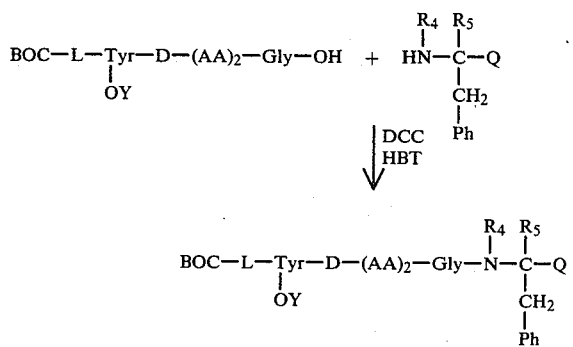

In the above reaction, Ph represents phenyl and Q is

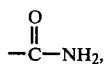

—CH$_2$OH, —CN,

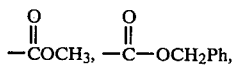

and other like groups.

When Q is

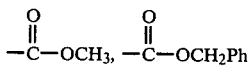

and other like ester groups, it can be converted, after coupling, to —CH$_2$OH by treatment with NaBH$_4$. This reduction technique is described in Yamamura et al., U.S. Pat. No. 3,700,651. When Q represents a benzyl ester or other ester comprising a group which is readily removable by hydrogenolysis, it can be converted to the free acid by hydrogenolysis in the presence of palladium on carbon. The free acid is convertible to the amide by treatment with ammonia in the presence of DCC and HBT.

The amide moiety can be dehydrated to the nitrile by treatment with p-toluenesulfonyl chloride and pyridine in accordance with the method described in Yamada et al., *Bull. of the Chem. Soc. of Japan*, 50, 1088–1093 (1977)

In preparing the compounds of this invention by the aforedescribed sequence, it is highly preferred to employ, as C-terminal reactant, a compound which contains the group Z of the intended final product.

Once the intended modified tetrapeptide having the C-terminal group has been prepared, the O-protecting group on the tyrosyl (if such is present can be removed by hydrogenolysis and the N-BOC protecting group by treatment with trifluoroacetic acid.

The above represents only one sequence for preparing compounds of this invention. Other sequences are available. Another method which can be employed involves the step-wise, sequential addition of single amino acids or derivatives thereof in construction of the peptide chain beginning with the carboxamide, alcohol, or nitrile terminal moiety. Reaction techniques such as those described above would be employed in this as well as any other contemplated preparative sequence.

A further method for preparing compounds of this invention is solid phase synthesis. In this method the C-terminal residue is attached to a suitable polymeric support, and the peptide is extended one residue at a time until the desired peptide, still attached to the polymer support, is synthesized. The peptide then is removed from the support by use of a suitable deblocking reagent. For example, the C-terminal moiety, protected at the α-amino by a t-butyloxycarbonyl group, is coupled to a benzhydrylamine polymer by DCC activation. The N-BOC group is removed by reaction of the polymer attached residue with trifluoroacetic acid in methylene chloride. The resulting salt is neutralized with a suitable tertiary amine, and the sequence repeated for addition of each successive amino acid. Upon completion of preparation of the intended peptide sequence, the blocked peptide is removed from the polymeric support by treatment with HF at 0° C. The product then can be purified by chromatography. The specific conditions of the synthesis, e.g., reaction times, reaction temperatures, wash times, reagents, protecting groups, and the like, are such as one of ordinary skill in the art of solid phase peptide synthesis would well recognize.

Cleavage of the peptide from the polymeric support achieves removal of all blocking groups with formation of the tetrapeptide intermediate. Since it is highly desirable to retain such protecting groups in conversion of the product to the nitrile compound, solid phase synthesis is not a desirable method for preparing compounds of this invention in which Z is —CN.

In certain of the compounds of this invention, one or more of the groups R$_1$, R$_2$, and R$_4$ are C$_1$–C$_3$ primary alkyl. In those instances, the appropriate N-substituted amino acid is employed in the preparative sequence. Any of the N-monosubstituted amino acids can be prepared by the same sequence which is depicted as follows using an N-protected amino acid as starting material:

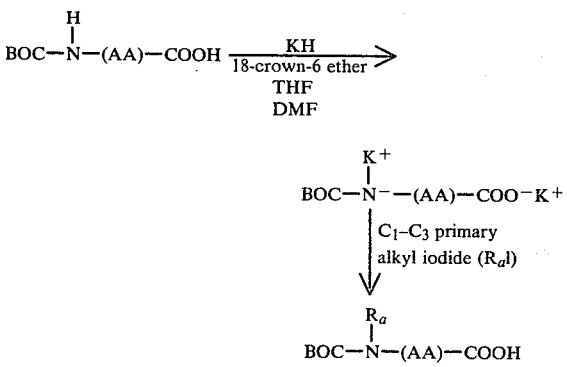

As the above sequence indicates, the N$^\alpha$-protected amino acid first is treated with potassium hydride in the presence of a suitable crown ether to generate the dianion. The intermediate then is treated with the appropriate alkyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino compound which is involved. Racemization can be minimized by using excess alkylating agent and by keeping the reaction time as short as possible. Nevertheless, even in the event that excessive racemization does occur, the product can be purified by recrystallization as the salt of a suitable chiral amine, for example, as the salt of d(+) α-phenylethylamine.

The resulting amino acid in which $R_4$ is $C_1$-$C_3$ primary alkyl can be converted to its corresponding amide, alcohol, or nitrile by any of the techniques described hereinabove.

In the instances in which both $R_1$ and $R_2$ are the same $C_1$-$C_3$ primary alkyl, the desired N,N-disubstituted tyrosine can be prepared by the following sequence:

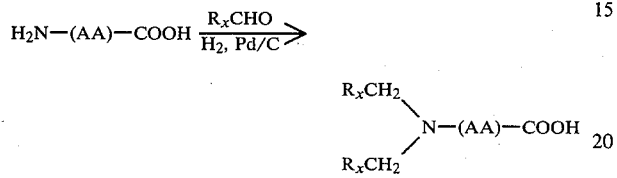

In the foregoing, $R_xCHO$ represents formaldehyde, acetaldehyde, or propionaldehyde.

In those instances in which $R_1$ and $R_2$ are different $C_1$-$C_3$ primary alkyl groups, the N,N-disubstituted tyrosine is available by treating the appropriate N-monosubstituted tyrosine, prepared in accordance with the foregoing sequence, with formaldehyde or acetaldehyde as described hereinabove.

In certain of the compounds of this invention, the group $R_5$ is $C_1$-$C_3$ primary alkyl. In those instances, the appropriate α-carbon substituted amino acid or its corresponding ester, amide, alcohol, or nitrile derivative is employed in the preparative sequence. The particular α-carbon substituted phenylalanine can be prepared using the method described by Stein et al., *Journal of the American Chemical Society*, Vol. 77, 700–703 (1955). Resolution of the racemic mixture is effected in accordance with Turk et al., *J. Org. Chem.*, Vol. 40, No. 7, 953–955 (1975). The resulting α-substituted phenylalanine can be converted to the corresponding amide, alcohol, or nitrile in accordance with the methods described hereinabove. This can be carried out either before or after it has been used in preparation of the tetrapeptide sequence; however, it is highly preferred that it be accomplished prior to preparation of the tetrapeptide.

Those compounds of this invention in which Y is acetyl are prepared from the corresponding peptide in which Y is hydrogen and the terminal amino group is suitably blocked. This latter compound is treated with acetic anhydride in the presence of pyridine to produce the corresponding N-blocked, O-acetyl peptide. Upon deblocking with a mixture of hydrochloric acid and acetic acid, the desired compound is obtained.

The compounds of this invention are valuable pharmaceutical agents. They exhibit analgesic activity, and they especially are useful upon parenteral administration to mammals, including humans.

The compounds of this invention can be administered as such, or they can be compounded and formulated into pharmaceutical preparations in unit dosage form for parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will produce an analgesic effect. Dose levels may range generally from about 0.1 milligram to about 100 milligrams per kilogram body weight of the recipient. The preferred dose range generally is from about 1.0 milligram to about 20 milligrams per kilogram body weight of the recipient.

The following examples are provided to illustrate the preparation and activity of the compounds of this invention. They are not intended to be limiting upon the scope thereof.

EXAMPLE 1

Preparation of L-Tyrosyl-D-alanyl-glycyl-$N^\alpha$-methyl-L-phenylalanylamide Acetate Salt A. Benzyl D-Alinate p-Toluenesulfonate To a mixture of 100 ml. of benzyl alcohol and 200 ml. of benzene containing 55.1 g. (0.29 mole) of p-toluenesulfonic acid monohydrate was added 25 g. (0.281 mole) of D-alanine. The mixture was brought to reflux, and water was removed azeotropically in a Dean-Stark apparatus. The mixture was heated for fifteen hours and then was cooled to room temperature and diluted with ether. The resulting precipitate was collected and recrystallized from methanolether to afford 55.3 g. (56%) of the title compound, m.p. 112°–115° C.

Analysis, calculated for $C_{17}H_{21}NO_5S$ (351.42): C, 58.10; H, 6.02; N, 3.99. Found: C, 58.19; H, 6.06; N, 3.82.

B. Benzyl $N^\alpha$-t-Butyloxycarbonyl-O-benzyl-L-tyrosyl-D-alinate

To 200 ml. of dry N,N-dimethylformamide (DMF) was added 35.1 g. (0.1 mole) of the product from Part A. The resulting mixture was stirred and cooled to 0° C., and 11.2 g. (0.1 mole) of diazabicyclooctane (DABCO) was added. The mixture was stirred for ten minutes at 0° C., and 37.1 g. (0.1 mole) of $N^\alpha$-t-butyloxycarbonyl-O-benzyl-L-tyrosine was added followed by 13.5 g. (0.1 mole) of 1-hydroxybenzotriazole (HBT) and 20.6 g. (0.1 mole) of N,N'-dicyclohexylcarbodiimide (DCC). The resulting mixture was stirred at 0° C. for three hours and then at room temperature for twenty-four hours. The mixture then was cooled to 0° C., the resulting suspension was filtered, and the filtrate was concentrated in vacuo. The resulting residue then was redissolved in ethyl acetate and was washed successively with 1 N $NAHCO_3$, water, 0.75 N cold citric acid, and water. The organic layer then was dried over magnesium sulfate, filtered, and concentrated in vacuo. The resulting residue then was dissolved in hot ethanol. Crystallization ensued upon cooling, After one recrystallization from ethanol, 41.5 g. (80%) of pure title compound was obtained, m.p. 121°–123° C.

Analysis, calculated for $C_{30}H_{36}N_2O_6$ (520.63): C, 69.21; H, 6.97; N, 5.38. Found: C, 68.99; H, 6.75; N, 5.17.

C. $N^\alpha$-t-Butyloxycarbonyl-O-benzyl-L-tyrosyl-D-alanine

To a mixture of 200 ml. of tetrahydrofuran (THF) and 20 ml. of water was added 31.2 g. (0.06 mole) of the product from Part B. The resulting solution was cooled to 0° C., and 13.2 ml. (1.1 equiv.) of 5 N sodium hydroxide was added slowly. The resulting mixture was stirred and allowed slowly to warm to room temperature.

After five hours, the mixture was partitioned between water and ether. The aqueous layer was separated and cooled, the pH was adjusted to 2 by addition of citric acid, and the mixture was extracted with ethyl acetate. The ethyl acetate extract was washed with water, dried over magnesium sulfate, filtered, and diluted with ether. The resulting precipitate was collected to afford 17.7 g (67%) of the title compound, m.p. 160°-162° C.

Analysis, calculated for $C_{24}H_{30}N_2O_6$ (442.51): C, 65.14; H, 6.83; N, 6.63. Found: C, 64.73; H, 6.70; N, 6.20.

D. Benzyl $N^\alpha$-t-Butyloxycarbonyl-O-benzyl-L-tyrosyl-D-alanyl-glycinate To 70 ml. of dry DMF was added 6.74 g. (0.02 mole) of the p-toluenesulfonic acid salt of benzyl glycinate. The resulting mixture was cooled to 0° C., and 2.24 g. (0.020 mole) of DABCO was added. The mixture was stirred for a few minutes, and 8.84 g. (0.020 mole) of the product of Part C was added followed by 2.7 g. (0.020 mole) of the HBT and 4.12 g. (0.020 mole) of DCC. The reaction mixture was stirred for two hours at 0° C. and then for twenty-four hours at room temperature. The resulting suspension was cooled to 0° C., filtered, and the filtrate was concentrated in vacuo. The resulting residue was dissolved in ethyl acetate and was washed successively with 1 N sodium bicarbonate, water, cold 0.75 N citric acid, and water. The organic phase was dried over magnesium sulfate, filtered, and concentrated in vacuo. The resulting residue was crystallized from ethanol to give 10.8 g. (92%) of pure title compound, m.p. 145°-147° C.

Analysis, calculated for $C_{33}H_{39}N_3O_7$ (589.69): C, 67.22; H, 6.67; N, 7.13. Found: C, 67.32; H, 6.83; N, 6.91.

E. $N^\alpha$-t-Butyloxycarbonyl-O-benzyl-L-tyrosyl-D-alanyl-glycine

To 150 ml. of a 9:1 mixture of tetrahydrofuran and water were added 15.95 gms. (27 mmoles) of the product from Part D. The mixture was cooled to 0° C. with stirring, and 30 ml. of 1 N sodium hydroxide were added dropwise to the resulting mixture. The mixture was stirred for 2 hours upon completion of the dropwise addition and then was extracted twice with ether. The separated aqueous layer was acidified to pH 2.5 by addition of 30 ml. of 1 N hydrochloric acid. The title compound crystallized, was collected by filtration, and was recrystallized once from a mixture of methanol and water and twice from ethyl acetate to give 11.43 gms. (85% theory), m.p. 104°-107° C. $[\alpha]_D^{25}+31.4°$ (C=0.5, MeOH).

Analysis, Calculated for $C_{26}H_{33}N_3O_7$ (499.54): C, 62.51; H, 6.66; N, 8.41. Found: C, 62.31; H, 6.83; N, 8.12.

F. $N^\alpha$-t-Butyloxycarbonyl-$N^\alpha$-methyl-L-phenylalanine, d-(+) α-methylbenzylamine salt To 75 ml. of tetrahydrofuran were added 13.26 gms. (0.05 moles) of $N^\alpha$-t-butyloxycarbonyl-L-phenylalanine. The resulting mixture was added dropwise over a 30 minute period to a mechanically stirred suspension of 0.15 mole of potassium hydride and 0.5 gram of 18-crown-6 ether at 0° C. under a nitrogen atmosphere. The mixture was stirred for an additional hour at 0° C. A solution of 6.23 ml. (0.1 mole) of methyl iodide in 15 ml. of tetrahydrofuran was added dropwise over a 15 minute period. The mixture was maintained for two hours, and a mixture of 10 ml. of acetic acid and 10 ml. of tetrahydrofuran was added dropwise followed by 20 ml. of ethanol. The mixture then was poured onto 400 ml. of ice. The pH of the resulting aqueous phase then was raised to 12-13 by addition of 2 N sodium hydroxide. The aqueous mixture was extracted twice with ether and then was acidified to pH 3.0 by addition of solid citric acid. The aqueous mixture then was extracted three times with 200 ml. of ether. The ether extracts were combined, extracted with water, dried over magnesium sulfate, and evaporated in vacuo to a syrup. The syrup was dissolved in 50 ml. of ether, and 6.44 ml. (0.05 moles) of d(+)-α-methylbenzylamine were added. The resulting solution was diluted with 350 ml. of hexane and was scratched. The product was collected by filtration to give 15.83 gms. (79% theory) of the title compound. Recrystallization from ethyl acetate gave 13.70 gms. (68% theory) of the title compound, m.p. 136°-139° C. $[\alpha]_D^{25}-28.2°$ (C=1, EtOH).

Analysis, Calculated for $C_{23}H_{32}N_2O_4$ (400.50); C, 68.97; H, 8.05; N, 6.99. Found: C, 68.75; H, 7.81; N, 6.74.

G. $N^\alpha$-t-Butyloxycarbonyl-$N^\alpha$-methyl-L-phenylalanyl amide $N^\alpha$-t-Butyloxycarbonyl-$N^\alpha$-methyl-L-phenylalanine (4.0 gms.; 0.01 moles; prepared by acidification of the d(+)-α-methylbenzylamine salt and extraction into ether) was dissolved in 20 ml. of N,N-dimethylformamide (DMF). The mixture was cooled to $-15°$ C., and 1.56 ml. (0.012 moles) of isobutyl chloroformate were added followed by 1.32 ml. (0.012 moles) of N-methylmorpholine. The reaction mixture was stirred for 10 minutes at $-15°$ C., and anhydrous ammonia was bubbled into the reaction mixture for 1.5 hours. The resulting mixture was stirred for one hour at $-15°$ C., and the mixture then was poured into a vessel containing 200 ml. of ice. The aqueous solution was extracted with ethyl acetate. The organic layer was separated and washed successively with 1.5 N citric acid, water, 1 N sodium bicarbonate and water. The ethyl acetate solution then was dried over magnesium sulfate and evaporated in vacuo to a syrup which was crystallized from a mixture of ether and petroleum ether to give 2.12 grams (76% theory) of the title compound, m.p. 91°-92° C. $[\alpha]_D^{25}-111.2°$ (C=0.5, CHCl$_3$).

Analysis, Calculated for $C_{15}H_{22}N_2O_3$ (278.33): C, 64.73; H, 7.97; N, 10.06. Found: C, 64.95; H, 7.81; N, 9.79.

H. $N^\alpha$-t-Butyloxycarbonyl-O-Benzyl-L-tyrosyl-D-alanyl-glycyl-$N^\alpha$-methyl-L-phenylalanyl amide To 20 ml. of freshly prepared glacial acetic acid containing anhydrous hydrogen chloride (1 N) and 2 ml. of anisole were added 1.95 gms. (0.007 moles) of $N^\alpha$-t-butyloxycarbonyl-$N^\alpha$-methyl-L-phenylalanyl amide. The resulting mixture was stirred at room temperature for 30 minutes. The mixture then was poured into ether, and the resulting precipitate was collected and dried (1.5 gms.). The hydrochloride salt then was dissolved in 30 ml. of DMF. The solution was cooled to 0° C., and 1.4 ml. (0.007 moles) of dicyclohexylamine were added. The mixture was stirred for a few minutes, and 3.5 gms. (0.007 moles) of $N^\alpha$-t-butyloxycarbonyl-O-benzyl-L-tyrosyl-D-alanyl-glycine, 950 mg. (0.007 moles) of HBT, and 1.4 gms. (0.007 moles) of DCC were added. The reaction mixture then was stirred at 0° C. for 2 hours and then at 4° C. for 24 hours. The mixture was cooled to 0° C. and filtered. The filtrate was concentrated in vacuo to an oil which was redissolved in ethyl acetate. The ethyl acetate solution was extracted successively with 1 N sodium bicarbonate, water, cold 0.75 N citric acid, and water. The organic phase was dried over magnesium sulfate and concentrated in vacuo to an oil. The oil was chromatographed on a 40 cm.×3 cm. column of Grace and Davison Grade 62 silica gel in chloroform. The product was eluted using a stepwise gradient of chloroform to a mixture of 10% methanol in chloroform. The product was isolated according to the thin-layer profile of the fractions collected to give 3.55 gms. (77% theory) of the title compound. $[\alpha]_D^{25} -9.2°$ (C=0.5, MeOH).

Analysis, Calculated for $C_{36}H_{45}N_5O_7$ (659.8): C, 65.54; H, 6.57; N, 10.61. Found: C, 65.46; H, 6.58; N, 10.36.

I.
$N^\alpha$-t-Butyloxycarbonyl-L-tyrosyl-D-alanyl-glycyl-$N^\alpha$-methyl-L-phenylalanyl amide The product from Part H (3.2 gms; 0.0485 moles) was dissolved in 60 ml. of ethanol, and 1.5 gms. of 5% palladium on carbon were added to the mixture as a water slurry. Nitrogen was bubbled into the reaction mixture through a gas dispersion tube for about 5 minutes followed by hydrogen gas for 6 hours. The reaction mixture then was flushed with nitrogen, and the palladium catalyst was removed by filtration. The mixture was concentrated in vacuo to a syrup. The syrup was dissolved in chloroform and absorbed onto a 40 cm.×3 cm. chromatographic column containing Grace and Davison Grade 62 silica gel. The product was eluted using a stepwise gradient of chloroform to 10% methanol in chloroform and was isolated according to the thin-layer profile of the fractions collected to give 2.0 gms. (74% theory). $[\alpha]_D^{25} -9.9°$ (C=0.5, MeOH).

Amino acid analysis, Found: Gly, 1.01; Ala, 0.99; Tyr, 0.99; $NH_3$, 1.14.

J.
L-Tyrosyl-D-alanyl-glycyl-$N^\alpha$-methyl-L-phenylalanyl amide, acetate salt The product from Part I (1.6 gms.; 0.00281 moles) was dissolved in 10 ml. of trifluoroacetic acid containing 0.5 ml. of anisole. The mixture was stirred at 0° C. for 30 minutes. The mixture then was poured into ether, and the resulting precipitate was collected and dried (1.1 gms.). The solid was dissolved in sufficient aqueous buffer solution (1% pyridine and 0.05% acetic acid) to make 15 ml., and the solution was applied to a 2.5 cm.×99 cm. column of DEAE-Sephadex A-25 (acetate) which had been equilibrated with the same buffer. The eluate was monitored at 280 nm, and the appropriate fractions were combined and lyophilized. Re-lyophilization from 10% acetic acid, followed by lyophilization from a 75:25 mixture of water and acetonitrile gave 0.84 gms. of the title compound. $[\alpha]_D^{25} +27.8°$ (C=1, 1 N HCl).

Amino acid analysis, Found: Tyr, 0.98; Ala, 1.03; Gly, 1.00; $NH_3$, 1.05.

EXAMPLE 2
Preparation of L-Tyrosyl-D-Alanyl-Glycyl-L-Phenylalanyl Amide Hydrochloride

A.
$N^\alpha$-t-Butyloxycarbonyl-O-benzyl-L-tyrosyl-D-alanyl-glycyl-L-phenlalanine, methyl ester To 30 ml. of DMF were added 2.5 gms. (0.005 moles) of $N^\alpha$-t-butyloxycarbonyl-O-benzyl-L-tyrosyl-D-alanyl-glycine (prepared as in Example 1) and 1.08 gms. (0.005 moles) of the hydrochloride salt of L-phenylalanine, methyl ester. The mixture was stirred at 0° C., and 0.99 ml. (0.005 moles) of dicyclohexylamine was added. The mixture was stirred for 5 minutes at 0° C., and 670 mg. (0.005 mmoles) of HBT and 1.03 gms. (0.005 moles) of DCC were added. Stirring was continued at 0° C. for 2 hours and then at room temperature for 48 hours. The reaction mixture was cooled to 0° C., and the resulting precipitate was collected. The filtrate was concentrated in vacuo. The residue was dissolved in ethyl acetate, and the ethyl acetate solution was extracted successively with 1 N sodium bicarbonate, water, 0.75 N citric acid, and water. The ethyl acetate solution was dried over magnesium sulfate and concentrated in vacuo. The resulting oil was crystallized from ether and recrystallized from ethyl acetate to give 2.7 grams (82%) of the title compound, m.p. 149°–152° C. $[\alpha]_D^{25} +22°$ (C=0.5, MeOH).

Analysis, Calculated for $C_{36}H_{44}N_4O_8$ (660.74): C, 65.44; H, 6.71; N, 8.48. Found: C, 65.51; H, 6.46; N, 8.53.

B.
$N^\alpha$-t-Butyloxycarbonyl-O-benzyl-L-tyrosyl-D-alanyl-glycyl-L-phenylalanyl amide To 35 ml. of methanol were added 1.2 grams (0.0018 moles) of the product from Part A. The solution was placed in a pressure bottle. The pressure bottle was cooled to 78° C. and 20 ml. of anhydrous ammonia were added. The bottle was sealed, and the mixture was stirred at room temperature for 48 hours. The bottle then was cooled, opened, and the ammonia was allowed to evaporate. The product was precipitated by addition of ether, and the mixture was filtered and dried to give 800 mg. (67%) of the title compound, m.p. 203°–204° C. $[\alpha]_D^{25} +14°$ (C=0.5 MeOH).

Analysis, Calculated for $C_{35}H_{43}N_5O_7$ (645.7): C, 65.10; H, 6.71; N, 10.85. Found: C, 65.09; H, 6.73; N, 10.88.

C.
$N^\alpha$-t-Butyloxycarbonyl-L-tyrosyl-D-alanyl-glycyl-L-phenylalanyl amide To a mixture of 20 ml. of DMF and 60 ml. of ethanol were added 700 mg. (0.011 moles) of the product from Part B. To the resulting solution was added 0.5 gram of 5% palladium on carbon as a slurry in DMF. Nitrogen was bubbled into the mixture through a gas dispersion tube for 5 minutes followed by hydrogen gas for 6 hours. The mixture then was flushed with nitrogen, and the palladium catalyst was removed by filtration. The filtrate was concentrated in vacuo to an oil. The oil was dissolved in chloroform and applied to a 2 cm.×10 cm. column containing Woelm Grade III silica gel. The column was eluted with an 80:20 mixture of chloroform and methanol to obtain, upon evaporation of solvent, 560 mg. (92%) of the title compound. $[\alpha]_D^{25}+14.9°$ (C=0.5, MeOH).

Analysis, Calculated for $C_{28}H_{37}N_5O_7$ (555.6): C, 60.53; H, 6.71; N, 12.60. Found: C, 60.83; H, 7.00; N, 12.34.

Amino acid analysis, Found: Gly, 0.99; Ala, 0.99; Tyr, 1.01; Phe, 1.00; NH$_3$, 0.98.

D.
L-Tyrosyl-D-alanyl-glycyl-L-phenylalanyl amide, hydrochloride salt

To 5 ml. of a mixture of 2 N gaseous hydrogen chloride in glacial acetic acid and containing 0.1 ml. of anisole were added 520 mg. (0.00093 moles) of the product from Part C. The mixture was stirred at room temperature for 20 minutes and then was freeze dried to give 460 mg. (100%) of the title compound. $[\alpha]_D^{25}+71.4°$ (C=0.5, 1 N HCl).

Analysis, Calculated for $C_{23}H_{30}N_5O_5Cl$: C, 56.15; H, 6.15; N, 14.24; Cl, 7.21. Found: C, 56.35; H, 6.18; N, 13.90; Cl, 7.11.

Amino acid analysis, Found: Tyr, 1.01; Ala, 0.99; Gly, 0.99; Phe, 0.99; NH$_3$, 1.05.

EXAMPLE 3

Preparation of
L-Tyrosyl-D-Alanyl-Glycyl-L-α-Methylphenylalanyl Amide, Acetate Salt.

A.
L-α-Methylphenylalanine, benzyl ester, tosylate salt

To 100 ml. of benzene were added 3.0 grams (0.0168 moles) of L-α-methylphenylalanine. To the resulting suspension then were added 3.5 grams (1.1 equiv.) of p-toluenesulfonic acid hydrate and 10 ml. of benzyl alcohol. The mixture was refluxed in the presence of a Dean-Stark water trap for four days. The mixture then was cooled to room temperature, and ether was added to precipitate the tosylate salt. The resulting precipitate was collected and dried to give 7.0 grams (94%) of the title compound, m.p. 129°–131° C. $[\alpha]_D^{25}-10.7°$ (C=0.5, 1 N MeOH).

Analysis, Calculated for $C_{24}H_{27}NO_5S$ (441.5): N, 3.17. Found: N, 2.87. B. N$^\alpha$-t-Butyloxycarbonyl-O-benzyl-L-tyrosyl-D-alanyl-glycyl-L-α-methyl-phenylalanine, benzyl ester To 80 ml. of DMF were added 5.74 grams (0.013 mmoles) of the product from Part A. The resulting mixture was cooled to 0° C. for 5 minutes, and 6.5 grams (13 mmoles) of N$^\alpha$-t-butyloxycarbonyl-O-benzyl-L-tyrosyl-D-alanyl-glycine (prepared as in Example 1), 1.8 grams (13 mmoles) of HBT, and 2.7 grams (13 mmoles) of DCC were added. The mixture was stirred at 0° C. for two hours and then at room temperature for 24 hours. The mixture then was cooled to 0° C., and the resulting precipitate was removed by filtration. The filtrate was evaporated in vacuo. The resulting residue was dissolved in ethyl acetate, and the ethyl acetate solution was extracted successively with 1 N sodium bicarbonate, water, 0.75 N citric acid, and water. The organic phase then was dried over magnesium sulfate and evaporated in vacuo to an oil. The oil was crystallized from ether and recrystallized from a mixture of ethyl acetate and ether to give 7.0 grams (72%) of the title compound. $[\alpha]_D^{25}+7.9°$ (C=0.5, MeOH).

Analysis, Calculated for $C_{43}H_{50}N_4O_8$ (750.86): C, 68.78; H, 6.71; N, 7.46. Found, C, 68.75; H, 6.46; N, 7.21.

C.
N$^\alpha$-t-Butyloxycarbonyl-L-tyrosyl-D-alanyl-glycyl-L-α-methylphenylalanine, dicyclohexylamine salt To 50 ml. of ethanol were added 4.0 grams (0.0053 moles) of the product from Part B. A slurry of 2.0 grams of 5% palladium on carbon in DMF then was added. Nitrogen was bubbled into the mixture through a gas dispersion tube for 5 minutes followed by hydrogen gas for 4 hours. The mixture then was flushed with nitrogen, and the palladium catalyst was removed by filtration. The filtrate was concentrated in vacuo to a syrup. The syrup in chloroform was applied to a 10 cm. × 2 cm. column contaning Grace and Davison Grade 62 silica gel. The column was eluted with a step gradient of chloroform→chloroform-methanol (9.5:0.5). The major fractions were combined, and the solvent was evaporated. The resulting oil was dissolved in ethyl acetate, and 1 ml. of dicyclohexylamine was added. The resulting precipitate was collected and dried to give 2.6 grams (65%) of the title compound, m.p. 142°–146° C. $[\alpha]_D^{25}+46.3°$ (C=0.5, MeOH).

D.
N$^\alpha$-t-Butyloxycarbonyl-L-tyrosyl-D-alanyl-glycl-L-α-methylphenylalanyl amide The product from Part C (2.0 grams; 0.0027 moles) was neutralized with a mixture of ethyl acetate and 0.75 N citric acid. The resulting organic layer was separated, extracted with water, dried over magnesium sulfate, and evaporated in vacuo to an oil (1.5 grams). The resulting free acid was dissolved in 30 ml. of DMF, and the solution was cooled to 0° C. in a pressure bottle. DCC (560 mg.; 0.0027 moles) was added, and the mixture was stirred for 4 hours at 0° C. and then for 3 hours at room temperature. The bottle then was cooled to −78° C., and 30 ml. of anhydrous ammonia were added. The bottle was again sealed, and the mixture was allowed to stir at room temperature for 48 hours. The mixture was cooled to −78° C., the bottle was opened, and ammonia was allowed to evaporate at room temperature. The solvent then was evaporated in vacuo. The resulting residue was dissolved in ethyl acetate, and the ethyl acetate solution was extracted first with 0.75 N citric acid and then with water. The solution was dried over magnesium sulfate, and the solvent was evaporated in vacuo. The residue was dissolved in chloroform and applied to a 3 cm.× 45 cm. column of Grace and Davison Grade 62 silica gel. The column was eluted with a step gradient comprising chloroform→chloroform:methanol (9:1). Fractions were combined on the basis of the TLC profile to give, after evaporation of solvent, 1.1 grams (72%) of the title compound. $[\alpha]_D^{25}-26°$ (C=0.4, MeOH).

Amino acid analysis, Found: Gly, 0.99; Ala, 1.00; Tyr, 0.99; NH$_3$, 1.12.

E.
L-Tyrosyl-D-alanyl-glycyl-L-α-methylphenylalanyl amide, acetate salt

To 20 ml. of a mixture of 1 N gaseous hydrogen chloride in glacial acetic acid and containing 0.3 ml. of anisole were added 900 mg. (0.0016 moles) of the product from Part D. The mixture was stirred at room temperature for 30 minutes and then was poured into ether. The resulting precipitate was collected and dried (720 mg.). The solid was dissolved in sufficient aqueous buffer solution (1% pyridine and 0.05% acetic acid) to achieve 5 ml. volume, and the solution was applied to a 2.5 cm.×99 cm. column of DEAE-Sephadex A-25 (acetate) previously equilibrated with the same buffer. The eluate was monitored at 280 nm, and appropriate fractions were combined and lyophilized. Re-lyophilization from 10% acetic acid followed by lyophilization from a 75:25 mixture of water and acetonitrile gave 400 mg. of the title compound. $[\alpha]_D^{25} + 23.9°$ (C=0.5, 1 N HCl).

Analysis, Calculated for $C_{26}H_{35}N_5O_7$ (529.60): C, 58.97; H, 6.66; N, 13.22; O, 21.15. Found: C, 59.02; H, 6.36; N, 12.99; O, 21.41.

Amino acid analysis, Found: Tyr, 0.96; Ala, 1.01; Gly, 1.00; $NH_3$, 1.03.

EXAMPLE 4

Preparation of
L-Tyrosyl-D-Alanyl-Glycyl-L-(2-Amino-3-phenyl-propanol), Acetate Salt

A.
$N^\alpha$-t-Butyloxycarbonyl-L-tyrosyl-D-analyl-glycyl-L-(2-amino-3-phenylpropanol)

$N^\alpha$-t-Butyloxycarbonyl-L-tyrosyl-D-alanyl-glycine, dicyclohexylammonium salt (2.9 gms; 0.005 moles) was suspended in ethyl acetate and neutralized by addition of cold 1.5 N citric acid. The resulting ethyl acetate layer was separated and extracted with water. The ethyl acetate solution then was dried over magnesium sulfate and concentrated in vacuo. The resulting solid was dissolved in 50 ml. of DMF, cooled to 0° C., and 750 mg. (0.005 moles) of L-(2-amino-3-phenylpropanol), 680 mg. (0.005 moles) of HBT, and 1.03 gms. (0.005 moles) of DDC were added to the mixture. The resulting mixture was stirred for 2 hours at 0° C., and the resulting precipitate was collected by filtration. The filtrate was concentrated in vacuo. The residue was dissolved in ethyl acetate, and the ethyl acetate solution was extracted successively with 1 N sodium bicarbonate, water, 0.75 N citric acid, and water. The ethyl acetate solution then was dried over magnesium sulfate and concentrated in vacuo. The residue was dissolved in chloroform and applied to a 3 cm.×45 cm. column of Grace and Davison Grade 62 silica gel. Elution was effected with a step gradient of chloroform→chloroform:methanol (9:1). Fractions were combined on the basis of the TLC profile to give, after evaporation of solvent, 900 mg. (33%) of the title compound. $[\alpha]_D^{25} + 9.2°$ (C=0.5, MeOH).

Analysis, Calculated for $C_{28}H_{38}N_4O_7$ (542.6): C, 61.98; H, 7.06; N, 10.33. Found: C, 61.75; H, 6.79; N, 10.10.

Amino acid analysis, Found: Gly, 1.00; Ala, 1.00; Tyr, 1.00.

B.
L-Tyrosyl-D-alanyl-glycyl-L-(2-amino-3-phenyl-propanol), acetate salt

To 10 ml. of trifluoroacetic acid containing 1 ml. of anisole were added 800 mg. (0.0147 moles) of the product from Part A. The mixture was stirred at 0° C. for 30 minutes. The mixture then was freeze-dried. The resulting freeze-dried solid was dissolved in sufficient aqueous buffer solution (1% pyridine: 0.05% acetic acid) to provide 10 ml., and the solution was applied to a 2.5 cm.×99 cm. column of DEAE-Sephadex A-25 (acetate) previously equilibrated with the same buffer. The eluate was monitored at 280 nm, and the appropriate fractions were combined and lyophilized. Re-lyophilization from glacial acetic acid followed by lyophilization from a 75:25 mixture of water and acetonitrile gave an oil which, after treatment with ether, crystallized. The resulting solid was filtered and dried to give 600 mg. (81%) of the title compound. $[\alpha]_D^{25} + 58.3°$ (C=0.5, 1 N HCl).

Analysis, Calculated for $C_{25}H_{34}N_4O_7$ (504.568): C, 59.75; H, 6.82; N, 11.15. Found: C, 59.69; H, 6.57; N, 11.38.

The compounds of this invention are useful as analgesics. The analgesic activity of the compounds of this invention is demonstrated by the mouse hot plate test. In this test, a mouse is placed inside an upright acrylic cylinder comprising, as its base, a hot plate surface which is maintained at 52° C. In this test, the mouse is given, by subcutaneous injection, a predetermined amount of test compound dissolved or suspended in a suitable carrier. A predetermined period subsequent to administration of the test compound is permitted to elapse, and the mouse then is placed on the hot plate surface. The latencies in seconds until the occurrence of each of two separate phenomena then are recorded. First, the latency until the mouse licks its hind paw is measured, and, secondly, the latency until the mouse jumps from the hot plate surface is measured. An agent which exhibits analgesic activity produces an increase in these latencies over those of control mice which receive injections only of the carrier. This must occur in a dose range which produces no motor incoordination or incapacitation. The following Tables record the results obtained from this test, comparing them with a saline control. Table I provides latency to hind paw lick, and Table II provides latency to escape jump. The criterion for an affirmative analgesic effect is as follows: the latency for the hind paw lick or escape jump for a treated animal must be equal to or greater than the mean control latency plus two standard deviations of the mean. Each result provided in the following Tables I and II represents the mean value plus or minus standard error.

TABLE I

Analgesic Activity
Latency to Hind Paw Lick, Seconds

| Compound[b] | Time Elapse min. | Control | Dose, mg/kg.[a] | | | | |
|---|---|---|---|---|---|---|---|
| | | | 0.3 | 1 | 3 | 10 | 30 |
| A | 15 | 25.8 ± 2.2 | — | 30.4 ± 2.6 | — | — | 113.9 ± 21.2[1] |
|   | 15 | 29.9 ± 2.6 | — | — | 35.5 ± 1.4[3] | 45.4 ± 2.9[1] | — |
|   | 30 | 27.7 ± 1.8 | — | — | — | 46.4 ± 4.8[1] | — |
|   | 60 | 27.7 ± 1.8 | — | — | — | 30.1 ± 2.7 | — |
| B | 15 | 29.2 ± 1.7 | — | — | 35.7 ± 2.3[3] | 63.4 ± 12.6[3] | — |
|   | 15 | 31.4 ± 1.7 | — | 34.8 ± 2.5 | 40.5 ± 2.7[2] | — | — |
|   | 30 | 29.8 ± 6.9 | — | — | — | 59.4 ± 10.0[3] | — |
|   | 60 | 29.8 ± 6.9 | — | — | — | 43.4 ± 6.1 | — |

TABLE I-continued

Analgesic Activity
Latency to Hind Paw Lick, Seconds

| Compound[b] | Time Elapse min. | Control | Dose, mg/kg.[a] | | | | |
|---|---|---|---|---|---|---|---|
| | | | 0.3 | 1 | 3 | 10 | 30 |
| | 15 | 25.0 ± 1.9 | 31.9 ± 1.9[3] | — | — | — | — |
| | 60 | 30.0 ± 2.6 | — | — | — | 37.0 ± 3.8 | — |
| | 90 | 30.0 ± 2.6 | — | — | — | 30.1 ± 3.9 | — |
| | 120 | 23.7 ± 1.4 | — | — | — | 29.6 ± 3.6 | — |
| | 120 | 28.0 ± 1.7 | — | — | — | 25.8 ± 1.6 | — |
| C | 15 | 26.6 ± 1.7 | — | — | 33.2 ± 2.2[3] | 114.4 ± 24.4[2] | — |
| | 15 | 31.4 ± 3.1 | — | 33.3 ± 2.2 | 48.1 ± 7.6[3] | — | — |
| | 15 | 33.4 ± 2.2 | — | — | — | 101.7 ± 15.9[1] | — |
| | 30 | 32.0 ± 2.7 | — | — | — | 71.2 ± 7.1[1] | — |
| | 60 | 28.2 ± 0.9 | — | — | — | 46.2 ± 6.3[2] | — |
| | 90 | 28.2 ± 0.9 | — | — | — | 32.0 ± 3.5 | — |
| | 15 | 26.9 ± 3.1 | 29.4 ± 2.7 | — | — | — | — |
| | 15 | 25.0 ± 1.9 | 34.0 ± 1.5[1] | — | — | — | — |
| | 120 | 28.0 ± 1.7 | — | — | — | 30.2 ± 2.9 | — |
| D | 15 | 26.8 ± 3.2 | — | — | 29.1 ± 2.4 | 35.7 ± 2.0[3] | — |
| | 15 | 29.6 ± 2.5 | — | 24.5 ± 1.5[3] | — | — | 63.5 ± 15.8[3] |
| | 30 | 29.7 ± 1.7 | — | — | — | 38.5 ± 5.0[2] | — |
| | 60 | 30.2 ± 2.1 | — | — | — | 27.3 ± 1.1 | — |

TABLE II

Analgesic Activity
Latency to Escape Jump, Seconds

| Compound[b] | Time Elapse, min. | Control | Dose, mg/kg.[a] | | | | |
|---|---|---|---|---|---|---|---|
| | | | 0.3 | 1 | 3 | 10 | 30 |
| A | 15 | 72.5 ± 9.2 | — | 74.7 ± 8.2 | — | — | 222.1 ± 12.6[1] |
| | 15 | 61.7 ± 5.7 | — | — | 97.1 ± 10.3[2] | 158.0 ± 8.4[1] | — |
| | 30 | 102.1 ± 9.7 | — | — | — | 148.2 ± 13.6[2] | — |
| | 60 | 102.1 ± 9.7 | — | — | — | 67.9 ± 9.0[2] | — |
| B | 15 | 43.8 ± 5.5 | — | — | 152.4 ± 17.5[1] | 226.2 ± 7.7[1] | — |
| | 15 | 62.9 ± 10.3 | — | 112.2 ± 21.2[3] | 144.3 ± 13.2[1] | — | — |
| | 30 | 73.8 ± 14.6 | — | — | — | 218.3 ± 16.4[1] | — |
| | 60 | 73.8 ± 14.6 | — | — | — | 89.4 ± 16.7 | — |
| | 15 | 63.7 ± 9.1 | 130.7 ± 15.8[1] | — | — | — | — |
| | 60 | 59.2 ± 5.8 | — | — | — | 84.3 ± 13.2[3] | — |
| | 90 | 59.2 ± 5.8 | — | — | — | 89.4 + 7.5[2] | — |
| | 120 | 79.4 ± 5.7 | — | — | — | 104.1 ± 5.8[2] | — |
| | 120 | 69.8 ± 4.2 | — | — | — | 126.4 ± 11.7[1] | — |
| C | 15 | 48.4 ± 4.7 | — | — | 133.1 ± 14.8[1] | 222.2 ± 9.1[1] | — |
| | 15 | 62.1 ± 9.1 | — | 126.5 ± 5.7[1] | 140.4 ± 19.0[1] | — | — |
| | 15 | 80.2 ± 7.4 | — | — | — | 237.3 ± 2.7[1] | — |
| | 30 | 60.2 ± 6.1 | — | — | — | 189.2 ± 12.8[1] | — |
| | 60 | 80.5 ± 8.8 | — | — | — | 105.0 ± 14.2 | — |
| | 90 | 80.5 ± 8.8 | — | — | — | 110.2 ± 9.8[3] | — |
| | 15 | 73.7 ± 6.9 | 126.2 ± 14.7[2] | — | — | — | — |
| | 15 | 63.7 ± 9.1 | 107.0 ± 8.1[1] | — | — | — | — |
| | 120 | 69.8 ± 4.2 | — | — | — | 104.7 ± 7.0[1] | — |
| D | 15 | 56.3 ± 6.9 | — | — | 109.4 ± 7.9[1] | 129.1 ± 8.8[1] | — |
| | 15 | 59.7 ± 6.8 | — | 92.2 ± 6.3[2] | — | — | 204.4 ± 13.6[1] |
| | 30 | 66.5 ± 7.2 | — | — | — | 65.2 ± 7.5 | — |
| | 60 | 86.5 ± 9.4 | — | — | — | 57.1 ± 9.1[2] | — |

Footnotes:

[a]The numerals "1", "2", and "3" appearing as superscripts indicate that the result is significant to $P<0.001$, to $P<0.01$, and to $P<0.05$, respectively.

[b]The designations refer to the following compounds:

A. L-Tyrosyl-D-alanyl-glycyl-L-phenylalanyl-amide hydrochloride.
B. L-Tyrosyl-D-alanyl-glycyl-L-α-methylphenyl-alanylamide acetate.
C. L-Tyrosyl-D-alanyl-glycyl-N$^α$-methyl-L-phenylalanylamide acetate.
D. L-Tyrosyl-D-alanyl-glycyl-L-(2-amino-3-phenylpropanol) acetate.

We claim:

1. A compound of the formula

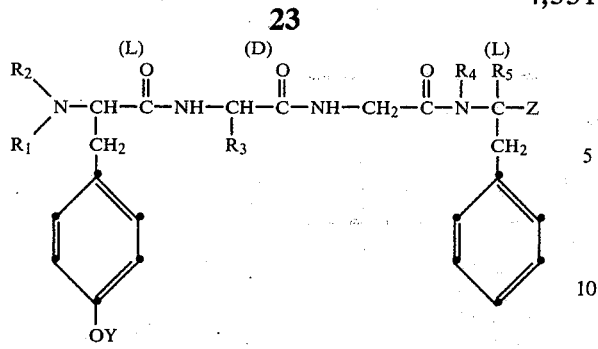

and pharmaceutically acceptable non-toxic acid addition salts thereof, in which L and D, when applicable, define the chirality;

$R_1$ and $R_2$ independently are hydrogen or $C_1$-$C_3$ primary alkyl;

$R_3$ is $C_1$-$C_4$ primary or secondary alkyl or —$CH_2CH_2$—S—$CH_3$;

$R_4$ is hydrogen;

$R_5$ is hydrogen or $C_1$-$C_3$ primary alkyl;

Y is hydrogen or acetyl; and

Z is

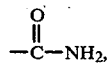

—$CH_2OH$, or —CN.

2. Compound of claim 1, in which Y is hydrogen.
3. Compound of claim 1, in which $R_1$ and $R_2$ are hydrogen.
4. Compound of claim 1, in which $R_3$ is methyl.
5. Compound of claim 1, in which $R_5$ is $C_1$-$C_3$ primary alkyl.
6. Compound of claim 5, in which $R_5$ is methyl.
7. Compound of claim 1, in which Z is

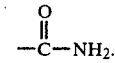

8. Compound of claim 1, in which Z is —$CH_2OH$.
9. Compound of claim 1, in which Z is —CN.
10. Compound of claim 7, in which Y is hydrogen.
11. Compound of claim 7, in which $R_1$ and $R_2$ are hydrogen.
12. Compound of claim 7, in which $R_3$ is methyl.
13. Compound of claim 7, in which $R_5$ is $C_1$-$C_3$ primary alkyl.
14. Compound of claim 7, in which $R_5$ is methyl.
15. Compound of claim 1, in which $R_3$ is $C_1$-$C_4$ primary or secondary alkyl.
16. Compound of claim 1, in which $R_3$ is —$CH_2CH_2$—S—$CH_3$.
17. Compound of claim 7, in which $R_3$ is —$CH_2CH_2$—S—$CH_3$.
18. Compound of claim 11, in which Y is hydrogen.
19. Compound of claim 18, in which $R_3$ is methyl.
20. Compound of claim 18, in which $R_3$ is —$CH_2CH_2$—S—$CH_3$.
21. Compound of claim 18, in which $R_5$ is $C_1$-$C_3$ primary alkyl.
22. Compound of claim 21, in which $R_5$ is methyl.
23. Compound of claim 22, in which $R_3$ is methyl.
24. Compound of claim 22, in which $R_3$ is —$CH_2CH_2$—S—$CH_3$.
25. Compound of claim 8, in which $R_1$ and $R_2$ are hydrogen.
26. Compound of claim 25, in which Y is hydrogen.
27. Compound of claim 26, in which $R_3$ is methyl.
28. Compound of claim 27, in which $R_5$ is methyl.
29. Compound of claim 9, in which $R_1$ and $R_2$ are hydrogen.
30. Compound of claim 29, in which Y is hydrogen.
31. Compound of claim 30, in which $R_3$ is methyl.
32. Compound of claim 31, in which $R_5$ is methyl.

* * * * *